United States Patent [19]

Garska et al.

[11] Patent Number: 4,499,316

[45] Date of Patent: Feb. 12, 1985

[54] CONVERSION OF EFFLUENT HYDROCARBONS STREAMS USING ALUMINOPHOSPHATE CATALYSTS

[75] Inventors: Daniel C. Garska, Saint Albans; Cyril B. Tellis, Charleston, both of W. Va.

[73] Assignee: Union Carbide Corporation, Danbury, Conn.

[21] Appl. No.: 596,598

[22] Filed: Apr. 4, 1984

[51] Int. Cl.³ ............................. C07C 3/10; C07C 3/20
[52] U.S. Cl. ..................................... 585/415; 208/70; 208/135; 585/322
[58] Field of Search .................. 208/70, 135; 585/415, 585/322

[56] References Cited

U.S. PATENT DOCUMENTS

| | | | |
|---|---|---|---|
| 2,507,625 | 5/1950 | Ehrhardt | 502/214 |
| 3,271,299 | 9/1966 | Kearby | 585/640 |
| 3,342,750 | 9/1967 | Kearby | 502/208 |
| 3,657,150 | 4/1972 | Juguin et al. | 585/671 |
| 4,132,669 | 1/1979 | Choca et al. | 502/208 |
| 4,179,358 | 12/1979 | Swift et al. | 502/64 |
| 4,385,994 | 5/1983 | Wilson et al. | 210/689 |

Primary Examiner—Delbert E. Gantz
Assistant Examiner—A. Pal
Attorney, Agent, or Firm—Gary L. Wamer

[57] ABSTRACT

By-product effluent streams from pyrolytic hydrocarbon cracking processes, containing monoolefins and diolefins, are treated to hydrogenate the olefins and to aromatize the aliphatics, with a catalyst comprising the aluminophosphates of U.S. Pat. No. 4,310,440.

14 Claims, No Drawings

CONVERSION OF EFFLUENT HYDROCARBONS STREAMS USING ALUMINOPHOSPHATE CATALYSTS

BACKGROUND OF THE INVENTION

1. Field of the Invention

This invention relates to the preparation of streams containing recoverable benzene, toluene, and xylenes ("BTX") from initial by-product effluent streams that contain other components, notably monoolefins and diolefins. In one aspect, the invention concerns the removal by conversion of these other components which ordinarily prevent recovery by distillation or solvent extraction of benzene-toluene-xylenes aromatics from the streams. In another aspect, it concerns a low severity process for treating the by-product streams with a specified catalyst, and under defined reaction conditions, both to produce benzene-toluene-xylenes from the initial stream and to reduce or eliminate those components that otherwise would interfere with the economic recovery of these aromatics from the streams.

1. Description of the Prior Art

The preparation of light olefins and diolefins, mainly ethylene, propylene, and butadiene, by the thermal pyrolysis, or cracking, of petroleum fractions is well know and widely practiced. (See for example, Kirk & Othmer's "Encyclopedia of Chemical Technology", Second Edition, Vol. 8, pp. 503-514.) In these pyrolitic cracking processes, hydrocarbons ranging from ethane, through LPG (liquefied petroleum gas, chiefly propane with a few percent butanes), naphtha, heavy gas oil, to even crude petroleum oil, are subjected to high temperature conditions, at low pressure and for a short time, to produce a maximum of the desired product. These thermal processes vary widely, and the yields from any one process depend not only on process equipment and conditions, but on such extraneous factors as the presence or absence of diluents and other reactants, e.g., oxygen, hydrogen, steam, etc.

Even the best of the pyrolitic processes is less than ideally selective. As a consequence, the total reactor effluent will contain not only the desired olefin or diolefin, but a variety of other components, ranging from methane gas to high boiling polycyclic hydrocarbons. These by-products are conventionally separated, usually by distillation and/or absorption, so as to concentrate the main desired products for ultimate recovery, and to produce one or more by-product effluent streams.

The by-product effluents contain a mixture of hydrocarbon types, including paraffins, monoolefins, diolefins, aromatics, cyclics, and various substituted and polynuclear aromatics. Unless the by-product effluent stream or streams contains a particularly valuable or desirable component, making removal economical, the by-product effluent streams are of only limited utility. The lighter gases are useful only as fuel, while the heavier, normally liquid, components usually termed "dripolene," or "pyrolysis gasoline" if not hydrogenated and then subjected to BTX extractions, are customarily either burned locally as fuel or else hydrogenated to saturate the unstable diolefins, and then blended with other gasoline fractions as motor fuel.

It has long been recognized that some of these by-product effluent streams, particularly the dripolene fractions, contain potentially valuable benzene, toluene, and xylenes (including ethylbenzene). Unfortunately, they also contain diolefins and monoolefins, which effectively interfere with most existing solvent extraction processes, such as the Udex and Sulfolane processes, for the extraction of aromatics from paraffins. Some of these olefins have boiling points similar to those of the BTX aromatics, and hence cannot be removed by fractional distillation. Selective hydrogenation to saturate the olefins and diolefins is practiced, and widely so, but the process tends to be expensive. Moreover, the diolefins in dripolene tend to be thermally unstable, forming catalyst-deactivating and exchanger-fouling carbonaceous deposits.

A variety of catalysts has been proposed for treating one or more of the by-product effluents from pyrolitic cracking processes so as to render the streams more valuable or more amenable to subsequent processing. (A tabulation of representative references identifying many of these processes, and many catalysts having conceivable useful activity for these processes, is appended.)

It is an object of the present invention to provide a process for preparing a stream from which benzene-toluene-xylenes may be recovered, by catalytically treating by-product effluent streams from pyrolytic hydrocarbon cracking processes. A further object is to provide a process for treating such by-product effluent stream in a simplified, low severity, operation so as both to produce benzene-toluene-xylenes (BTX), and, simultaneously, to decrease the content of interfering components. Still another object is to remove those monoolefins and diolefins which have heretofore interfered with the solvent extraction of BTX from dripolene and the like.

SUMMARY OF THE INVENTION

Briefly, in accordance with the invention, a stream from which benzene, toluene, and xylenes may be recovered readily is prepared by contacting a pyrolitic hydrocarbon cracking by-product effluent stream, containing substantial amounts of interfering monoolefins and diolefins, with an aluminophosphate molecular sieve catalyst under low severity hydrocarbon processing conditions. As a result of this treatment, not only are some olefins hydrogenated to non-interfering aliphatics, but a substantial fraction of the aliphatics is dehydrocyclized to benzene-toluene-xylenes.

One of the remarkable aspects of the invention is that the low severity conditions of temperature, pressure, and space velocity, which are suitable for hydrogenation with the aluminophosphate molecular sieve catalysts are also suitable in most instances for the cyclization and dehydrogenation involved in the aromatization using the aluminophosphate catalysts described in U.S. Pat. No. 4,310,440.

Thus, a simple processing scheme, with only a single reactor stage, is often adequate both to reduce to a minimal content, or eliminate the olefinic constituents that would interfere with the economic recovery of aromatics and produce benzene-toluene-xylenes from the feed stream.

A further important advantage of the invention resides in its ability to process any of a variety of the by-product effluent streams from pyrolitic cracking processes. As set out more fully below, these by-product effluent streams customarily include a $C_4$ fraction composed predominantly of butanes, butenes, and butadiene; a $C_5$ fraction composed mainly of pentanes, pentenes, pentadienes and cyclic $C_5$ compounds; a $C_6$–$C_8$ "dripolene" fraction containing BTX aromatics together with interfering olefins (i.e., having a similar boiling range); and a $C_9$-plus fraction, including some BTX along with higher alkylated benzenes and polynuclear aromatics and aliphatics. Each of these streams, plus others that may be present in a particular plant may be processed according to the invention.

The term "aluminophosphate" catalysts for use with the present invention refers to and is defined as those described aluminophosphates disclosed in U.S. Pat. No. 4,310,440. Various other aspects of the invention are set out below.

DETAILED DESCRIPTION OF THE INVENTION

Pyrolitic Cracking Processes

Pyrolitic cracking processes for the preparation of light olefins and diolefins such as ethylene, propylene, and/or butadiene, have been described in the literature, and accordingly no detailed exposition is called for here.

In essence, the thermal pyrolysis, or cracking, of petroleum fractions may utilize as feed stocks hydrocarbons such as ethane, LPG (liquefied petroleum gas, chiefly propane with a few percent butanes), naphtha, heavy gas oil, or crude petroleum oil. These are subjected to controlled high temperature, low pressure, short time, pyrolitic cracking to produce the desired product or products. Thereafter the reactor effluent is subjected to a combination of condensation, fractional distillation, absorption, and perhaps other unit operations, to segregate various effluent streams enriched in one or more desirable components. The precise arrangement of product recovery streams forms no part of the present invention, and indeed it is probable that no two pyrolitic cracking plants utilize the same recovery scheme.

For example, the reactor effluent liquid may be subjected to fractional distillation to separate one or more fractions rich in benzene (B.P. 80.103° C.), toluene (B.P. 110.623° C.), and/or the xylenes, namely ethylbenzene (B.P. 136.187° C.), p-xylene (B.P. 138.348° C.), m-xylene (B.P. 139.102° C.), and o-xylene (B.P. 144.414° C.). This fraction, or fractions is desirably solvent extracted, as for example by the UDEX or SULFOLANE process, to recover the BTX aromatic/aromatics.

In the absence of prior treatment, such as by the process of the present invention, solvent extraction is ineffective to extract the aromatics from the remaining aliphatics, inasmuch as solvents selective for aromatics will also extract many olefins and diolefins. However, the diolefins and the aromatics cannot be separated by fractional distillation; for example, benzene, with a boiling point of 80.103° C., is not easily distilled from the 2,4-hexadienes, which boil at about 80.0° C. Similarly, the various dimethylpentenes boil within a range of 72.2° C. to 85.0° C.

Be that as it may, and howsoever produced or constituted, there inevitably will be one or more by-product effluent streams which contain diverse mixtures of hydrocarbon (and perhaps non-hydrocarbon) components, varying both the respect to boiling point and chemical classification. It is this diversity that either complicates or prevents the recovery of useable components.

By way of example in an illustrative pyrolitic cracking plant, the total reactor effluent may be segregated into a predominantly gaseous fraction including recoverable ethylene and propylene; a crude $C_4$ fraction, a distillation cut which includes hydrocarbons with primarily four carbon atoms each; a crude $C_5$ fraction, another distillation cut which primarily contains hydrocarbon molecules with five carbon atoms each, and generally containing a large quantity of unsaturated and cyclic compounds, including olefins and lesser amounts of $C_4$'s and lighter $C_6$'s and heavier, a $C_6$–$C_8$ fraction, sometimes referred to as pyrolysis gasoline or dripolene: and a $C_9$ plus fraction, a heavier distillation cut which primarily includes hydrocarbons with at least nine carbon atoms, along with lesser amounts of $C_5$–$C_8$ hydrocarbons. The $C_9$ fraction generally is produced as the distillation bottoms from the processing of dripolene to remove pyrolysis gasoline, and contains components as widely varying as styrene, ethyltoluenes, and trimethylbenzenes, to heavier compounds including ethylnaphthalene, diphenyl, and dimethylnaphthalene.

An illustrative $C_4$ fraction, giving both the range and a typical composition, is set out in Table I below:

TABLE I

| | Illustrative $C_4$'s Composition | |
|---|---|---|
| Compound | Observed Range | Typical Composition |
| Lights | 0.4–5.0 wt % | 1.1 |
| Methylacetylene, Propadiene | 0.1–1.0 | 0.7 |
| n & i-Butane | 2.1–15.0 | 3.8 |
| 1-Butene and Isobutylene | 20.0–39.0 | 33.8 |
| t-2-Butene | 4.0–7.0 | 5.7 |
| c-2 Butene | 3.0–5.0 | 4.5 |
| 1,3-Butadiene | 41.0–54.0 | 44.6 |
| Vinylacetylene | 0.4–1.5 | 0.7 |
| Ethylacetylene | 0.1–0.5 | 0.2 |
| $C_{5+}$ | 0.2–5.0 | 4.1 |

Illustrative $C_5$ compositions, from two different plants, "A" and "B", are likewise represented in Table II, below:

TABLE II

| | Illustrative $C_5$'s Composition | | | |
|---|---|---|---|---|
| | Plant A | | Plant B | |
| Compound | Observed Range | Typical Composition | Observed Range | Typical Composition |
| $C_4$ and Lighter | 0–1.5 wt % | 0.7 | 1.4–8.1 | 5.5 |
| n & i Pentanes | 0–14.4 | 7.2 | 17.3–44.6 | 23.6 |
| $C_5$ Olefins | 0.1–11.3 | 4.6 | 6.6–37.4 | 9.9 |
| Pentadienes | 9.7–35.3 | 20.0 | 3.5–12.9 | 4.2 |
| Isoprene | 2.4–43.0 | 13.1 | 5.0–16.8 | 5.9 |
| Cyclopentane | 1.6–7.5 | 3.2 | 0–2.0 | — |
| Cyclopentene | 2.2–10.3 | 5.4 | 2.0–14.4 | 2.3 |
| Cyclopentadiene | 0.60–2.8 | 1.4 | 1.0–20.6 | 4.6 |
| $C_6$ Paraffins | 1.1–7.2 | 4.2 | 1.3–10.5 | 10.1 |
| $C_6$ Olefins | — | — | 0–3.0 | 0.2 |
| Benzene | 0.4–5.1 | 1.3 | 0.23.8 | 23.8 |
| Dicyclopentadiene | 19.3–48.1 | 32.1 | 1.0–21.0 | 1.8 |
| Other $C_{6+}$ | 1.5–14.8 | 6.8 | 0–9.0 | 8.1 |

A C-Dripolene stream has a composition illustrated by the following composition of Table III.

TABLE III

| Illustrative C-Dripolene Composition | |
|---|---|
| Compound | Typical Composition |
| $C_4$ and Lighter | 1.3 |
| $C_5$ Paraffins | 1.0 |

TABLE III-continued

| Illustrative C-Dripolene Composition | |
|---|---|
| Compound | Typical Composition |
| $C_5$ Olefins | 4.5 |
| $C_5$ Diolefins | 0.6 |
| Cyclic $C_5$ Compounds | 6.4 |
| $C_6$–$C_9$ Aliphatics | 3.3 |
| Benzene | 43.6 |
| Toluene | 11.6 |
| Ethylbenzene and Mixed Xylenes | 4.5 |
| Styrene | 5.5 |
| Dicyclopentadiene | 9.4 |
| $C_9$ Aromatic Compounds | 4.1 |
| Other $C_{10}+$ Hydrocarbons | 4.3 |

Illustrative $C_9$ compositions, again from Plant "A" and Plant "B" are described in Table IV below:

TABLE IV

| | Illustrative $C_9$'s Composition | | | |
|---|---|---|---|---|
| | Plant A | | Plant B | |
| Compound | Observed Range | Typical Composition | Observed Range | Typical Composition |
| $C_5$–$C_8$ Nonaromatics | 0.5–4.4 | 0.5 | 0.2–3.4 | 0.2 |
| BTX | 0–9.8 | 1.7 | 0–31.9 | 1.2 |
| Styrene | 0.3–10.0 | 1.8 | 0–16.8 | 5.0 |
| Dicyclopentadiene | 7.2–40.0 | 29.2 | 4.7–42.0 | 40.5 |
| Methyl dicyclopentadiene and Dimethyldicyclopentadiene | 4.4–21.2 | 4.4 | 0–6.5 | 1.6 |
| Methyl Styrenes | 2.3–19.0 | 6.8 | 0–15.0 | 3.6 |
| $C_3$ Benzenes* | 8.0–26.0 | 12.7 | 0–12.5 | 7.3 |
| Indane | 0.2–16.9 | 13.8 | 0–6.9 | 0.2 |
| Indene | 3.9–15.6 | 9.9 | 1.0–13.0 | 9.8 |
| Naphthalenes | 0.6–9.3 | 3.5 | 3.0–15.0 | 14.1 |
| Other $C_{10+}$ | 10.7–32.6 | 15.7 | 14.6–48.6 | 16.7 |

*propyl benzenes, ethyl toluenes and trimethylbenzenes.

It will be appreciated, as noted earlier, that these compositions may vary quite widely, depending upon the initial feed to the pryrolitic cracking unit, the type of pyrolitic cracking unit, conditions in the pyrolitic unit, and the type and conditions of the product recovery section. The by-product effluent streams may likewise be blended with each other where this is desired, or may include recycle components from elsewhere in the product recovery section.

The aluminophosphate catalyst employed herein are described in U.S. Pat. No. 4,310,440. The crystalline aluminophosphates of U.S. Pat. No. 4,310,440 are generally described as having a framework structure whose chemical composition expressed in terms of mole ratios of oxides is:

$Al_2O_3$: 1.0±0.2 $P_2O_5$ each of said framework structures being microporous in which the pores are uniform and have nominal diameters within the range of about 3 to about 10 Angstroms, an intracrystalline adsorption capacity for water at 4.6 torr and 24° C. of at least 3.5 weight percent, the adsorption and desorption of water being completely reversible while retaining the same essential framework topology in both the hydrated and dehydrated state. The physical form of the aluminophosphate catalyst depends on the type of catalytic reactor being employed and may be in the form of a granule or powder, and is desirably compacted into a more readily usable form (e.g., larger agglomerates), usually with a silica or alumina binder for fluidized bed reaction, or pills, prills, spheres, extrudates, or other shapes of controlled size to accord adequate catalyst-reactant contact. As indicated, the catalyst may be employed either as a fluidized catalyst, or in a fixed or moving bed, and in one or more reaction stages.

Conversion Parameters

The conversion parameters, while broad, may be selected to provide a high degree of versatility, depending upon the feed composition and on the desired product quality.

With respect to temperature, a temperature within the range of about 300°–700° C., more preferably within the range of about 350°–600° C., is adequate for many, if not all, conversions. Higher temperature give more rapid and more complete reaction, but tend to produce undesirable by-products, chiefly coke, and may otherwise disturb the optimum balance of product composition with on-stream ease of operation.

The pressure, almost uniquely, is desirably quite low. Atmospheric pressure operation has been used successfully in the laboratory, but under specific conditions may be as high as 100 atmospheres or more. A desirable range is from atmospheric pressure to about 7 atmospheres. High pressures facilitate hydrogenation; lower pressures facilitate dehydrocyclization. The optimum pressure will therefore depend on process economics, considering whether it is more desirable to hydrogenate olefins than to produce a high yield of BTX aromatics.

Process stream flow rate, as expressed in units of weight hourly space velocity (WHSV), or weight of hydrocarbon feed per unit weight of catalyst, is suitably within the range of about 0.1 to about 20, more desirably about 0.5–5.0. High WHSV's permit more economic plant construction, while lower WHSV's permit more complete reaction at given temperature-pressure conditions.

If desired, a gaseous or gasifiable diluent may be introduced along with the hydrocarbon feed to the aluminophosphate catalyst. This diluent may be inert, typified by steam, nitrogen or a low boiling paraffin and mixtures thereof, or may be reactive with the feed under analysis conditions (e.g., hydrogen). Hydrogen is particularly desirable as it minimizes coke formation and deposition on the catalyst, with resulting premature deactivation, and also facilitates hydrogenation, as demonstrated below, however, the techniques of the present invention need not utilize hydrogen.

If either an inert or a reactive gas is employed, diluent/hydrocarbon molar (gas volume) ratios, optimally, of from about 0.1 to about 10 may be employed.

It is usually necessary that the catalyst be regenerated, either periodically or continuously, to remove the carbonaceous coke-like deposits from the catalyst. In a fluidized bed operation, a portion of the catalyst is continuously withdrawn from the reactor and then subjected to regeneration by combustion with air or other oxygen containing gas, after which it is continuously recycled to the reactor. In a moving bed operation, the removal of catalyst followed by regeneration may be effected either continuously or periodically. In a fixed bed operation, it is generally desirable that two or more reactors be used in parallel, so that when one is processing the hydrocarbon feed, the other is out of service and being regenerated. Regeneration conditions of approximately 450°–650° C., preferably 500°–600° C. may be employed.

EXPERIMENTAL PROCEDURE

Examples 1 to 9 were carried out using a hydrocarbon effluent from a thermal pyrolysis unit comprising a crude butadiene hydrocarbon effluent having the following analysis:

| CRUDE BUTADIENE COMPOSITION | |
|---|---|
| | Weight Percent |
| $C_3$ and lighter | 1.24 |
| Isobutane | 2.57 |
| n-Butane | 8.68 |
| 1-Butene and Isobutene | 33.74 |
| t-2-Butene | 4.15 |
| c-2-Butene | 2.44 |
| 1,3 Butadiene | 45.72 |
| $C_4$ Acetylenes | 1.28 |
| $C_{5+}$ Hydrocarbons | 0.19 |

Examples 1 to 9 were carried out using a modified Chromalytics Model MP-3 Thermal Chromatograph. The aluminophosphate catalyst was activated (activation of 0.25 gram of the aluminophosphate catalyst in the form of a powder by placing the catalyst in the reaction chamber (6 mm O.D.) between two plugs of glass wool) in situ at 550° C. in an air purge for one hour prior to use in the examples. The catalyst was cooled and was then purged with helium. The temperature of the reaction chamber and aluminophosphate catalyst was increased to 450° C. at which point the flow of helium was discontinued and the crude butadiene feed contacted with the aluminophosphate catalyst at 5 cubic centimeters per minute (cc/min) for ten minutes. The products were collected in a liquid nitrogen trap (POROPAK Q-SE 30) and the products were collected for the same time frame for each aluminophosphate catalyst after the butadiene feed had contacted the aluminophosphate catalyst. The butadiene feed was then discontinued and a helium purge begun. The nitrogen trap was then backflushed and rapidly heated to 200° C. The desorbed products are analyzed by vapor phase chromatograph using either a 30 ft. or 40 ft. OV-101 column at a helium flow of 20 cc/min and at a column temperature program of 4° C./minute from ambient temperature to 200° C. The vapor phase chromatograph was equipped with a flame ionization detector and a thermal conductivity detector and the results compiled by a PDP-1134 minicomputer interfaced directly to the gas chromatograph. The results of examples 1–9 are reported as weight percent and were derived from the area percents. The weight percents are deemed to have an accuracy of ±5 percent.

The procedure for example 5 was as employed for examples 1 to 4 except that the crude butadiene feed was saturated with water at ambient temperature prior to introduction to the reactor. The procedure of examples 6, 7 and 8 was the same as examples 1 to 4 except the reactor temperatures were 500° C., 550° C. and 500° C., respectively. The procedure for example 9 was the same as examples 1 to 4 except a gas sample was taken in a stainless steel sample bomb for GC-MS analysis (gas chromatograph—mass spectroscopy) after ten minutes, after which the procedure for examples 1 to 4 was followed.

EXAMPLES 1 TO 4

In examples 1 to 4, $AlPO_4$-5, $AlPO_4$-11, $AlPO_4$-14 and $AlPO_4$-31 were employed as catalysts at a temperature of 450° C., at ambient pressure and by introducing the crude butadiene at a rate of 5 cc/min (space velocity of 2.7 grams of feed per gram of catalyst per hour). The products were analyzed by vapor phase chromatography and had the following analysis, as shown in Table V:

TABLE V

| | Weight Percents | | | |
|---|---|---|---|---|
| Compounds | Example 1 AlPO —5 | Example 2 AlPO —11 | Example 3 AlPO 14 | Example 4 AlPO —31* |
| $C_1$-$C_4$ | 86.5 | 80.6 | 80.9 | 39.4 |
| $C_5$ + $C_6$ Aliphatics | 0.9 | 5.7 | 2.8 | 2.8 |
| Benzene | 0.1 | 0.4 | 0.3 | 0.4 |
| $C_7$ Aliphatics | 0.4 | 0.5 | 0.4 | 0.4 |
| Toluene | 0.1 | 0.7 | 0.1 | 0.5 |
| $C_8$ Aliphatics | 1.2 | 3.3 | 7.2 | 11.3 |
| Ethylbenzene, Xylenes | 8.1 | 6.1 | 4.5 | 26.4 |
| $C_{9+}$ Hydrocarbons | 2.7 | 2.7 | 3.8 | 18.6 |

*Average of three runs

EXAMPLE 6

$AlPO_4$-31 was evaluated as in examples 1 to 4, except that the crude butadiene feed was saturated with water at ambient temperature (18° C. to 22° C.) prior to contacting it with $AlPO_4$-31. Analysis of the products gave the following:

| Compounds | Weight Percents |
|---|---|
| $C_1$-$C_4$ | 53.2 |
| $C_5$ + $C_6$ Aliphatics | 6.2 |
| Benzene | 0.8 |
| $C_7$ Aliphatics | 2.7 |
| Toluene | 1.2 |
| $C_8$ Aliphatics | 24.2 |
| Ethylbenzene, Xylenes | 1.8 |
| $C_{9+}$ Hydrocarbons | 9.9 |

The above analysis when compared against example 4, supra, demonstrates the presence of diluent water resulted in an increase in $C_1$-$C_4$ compounds and an increase in $C_8$ aliphatics with a corresponding decrease in ethylbenzene/xylenes and $C_{9+}$ hydrocarbons.

EXAMPLES 6 & 7

$AlPO_4$-11 was evaluated as in examples 1 to 4 but at 500° C. (example 6) and at 550° C. (example 7). Analysis of the products in weight percents gave the following:

| Compounds | Example 6 | Example 7 |
|---|---|---|
| $C_1$-$C_4$ |  | 30.8 |
| $C_5$ + $C_6$ Aliphatics | 75.4 | 18.4 |
| Benzene | 0.1 | 7.9 |
| $C_7$ Aliphatics | 1.1 | 3.0 |
| Toluene | 0.8 | 8.6 |
| $C_8$ Aliphatics | 8.5 | 12.9 |
| Ethylbenzene, Xylenes | 10.4 | 11.5 |
| $C_{9+}$ Hydrocarbons | 3.6 | 7.0 |

EXAMPLE 8

$AlPO_4$-31 was evaluated as in examples 1 to 4 except that the crude butadiene feed was contacted with the $AlPO_4$-31 at 500° C. Analysis of the products gave the following:

| Compounds | Weight Percents |
|---|---|
| $C_1$-$C_4$ | 52.0 |
| $C_5$ + $C_6$ Aliphatics | 6.6 |
| Benzene | 1.3 |
| $C_7$ Aliphatics | 1.5 |
| Toluene | 1.6 |
| $C_8$ Aliphatics | 9.6 |
| Ethylbenzene, Xylenes | 21.0 |
| $C_{9+}$ Hydrocarbons | 6.4 |

EXAMPLE 9

$AlPO_4$-31 was evaluated according to the procedure employed for examples 1 to 4 with products after 10 minutes being analyzed by GC-MS. The GC-MS analysis of these products were as follows:

| Compounds | Weight Percents |
|---|---|
| $H_2/CH_4$ | 1.46 |
| $CO_2$ | 0.21 |
| $C_2H_6$ | 0.02 |
| $H_2O$ | 1.52 |
| $C_3H_4$ | 1.03 |
| $C_3H_6$ | 0.30 |
| $C_3H_8$ | 0.53 |
| $C_4H_6$ | 44.13 |
| $C_4H_8$ | 43.85 |
| $C_4H_{10}$ | 11.41 |

The total products analysis of the product was:

| Compounds | Weight Percent |
|---|---|
| Hydrogen/Methane | 0.4 |
| Ethane | 0.01 |
| $CO_2$ | 0.1 |
| $H_2O$ | 0.4 |
| Propane | 0.1 |
| Propylene | 0.1 |
| Propadiene/Methyl acetylene | 0.3 |
| Butane | 3.1 |
| Butenes | 11.3 |
| Butadiene | 11.4 |
| $C_5$-$C_6$ Aliphatics | 2.2 |
| Benzene | 0.3 |
| $C_7$ Aliphatics | 0.5 |
| Toluene | 0.4 |
| $C_8$ Aliphatics | 17.9 |
| Ethylbenzene, Xylenes | 27.4 |
| $C_9$ + Hydrocarbons | 24.2 |

EXAMPLE 10

The $AlPO_4$-11 (example 1), $AlPO_5$ (example 3) and $AlPO_4$-31 (example 4) catalysts employed in examples 1, 3 and 4 were subjected to x-ray analysis and the x-ray powder diffraction patterns compared with the x-ray diffraction patterns of calcined compositions which had not been used in the hydrocarbon conversions of the instant invention. A comparison of the x-ray powder diffraction patterns showed similar patterns which demonstrates the stability of the aluminophosphate compositions for the hydrocarbon conversion process of the instant invention.

We claim:

1. A low severity process for the preparation of a benzene-toluene-xylenes enriched stream containing minimal monoolefin and diolefin content, from a feed stream comprising a by-product effluent of a process for the pyrolitic cracking of hydrocarbons to produce light olefins or diolefins, said by-product effluent stream containing olefins and diolefins, said process comprising contacting said by-product effluent stream, under low severity conditions including a temperature within the range of about 300°–700° C., a pressure within the range of about 0 to 100 atmospheres, and a weight hourly space velocity within the range of about 0.1 to about 20, with a catalyst comprising at least one aluminophosphate molecular sieve.

2. Process of claim 1 wherein said conditions include a temperature within the range of about 350°–600° C., a pressure within the range of about 0–7 atmospheres, and a weight hourly space velocity within the range of about 0.5–5.0.

3. Process of claim 1 wherein said by-product effluent comprises a $C_4$ stream.

4. Process of claim 1 wherein said by-product effluent comprises a $C_5$ stream.

5. Process of claim 1 wherein said by-product effluent comprises a whole or fractionated dripolene or pyrolysis gasoline stream.

6. Process of claim 1 wherein said feed stream is admixed with a diluent.

7. Process of claim 6 wherein said diluent is water.

8. Process of claim 6 wherein said diluent is hydrogen.

9. Process of claim 6 wherein said diluent is a low boiling paraffin.

10. Process of claim 6 wherein said diluent is a mixture of a low boiling paraffin, hydrogen and/or steam.

11. Process of claim 1 wherein the aluminophosphate is $AlPO_4$-5.

12. Process of claim 1 wherein the aluminophosphate is $AlPO_4$-11.

13. Process of claim 1 wherein the aluminophosphate is $AlPO_4$-14.

14. Process of claim 1 wherein the aluminophosphate is $AlPO_4$-31.

* * * * *

UNITED STATES PATENT AND TRADEMARK OFFICE
CERTIFICATE OF CORRECTION

PATENT NO. : 4,499,316
DATED : Feb. 12, 1985
INVENTOR(S) : Daniel C. Garska and Cyril B. Tellis It is certified that error appears in the above—identified patent and that said Letters Patent is hereby corrected as shown below:

Col. 1, line 27 "know" should be -- known --.

Col. 4, line 32 in Table I, in middle column "2.1-15.0" should be -- 2.4-15.0 --.

Col. 5, line 45 "catalyst" to -- catalysts --.

Col. 6, line 12 "temperature" to -- temperatures --.

Col. 8, line 27 in Table V:

Change "AlPO-5" to -- $AlPO_4$-5";

Change "AlPO-11" to -- $AlPO_4$-11";

Change "AlPO 14" to -- $AlPO_4$-14"; and

Change "AlPO-31*" to -- $AlPO_4$-31*".

Signed and Sealed this

Twenty-seventh Day of August 1985

[SEAL]

Attest:

DONALD J. QUIGG

Attesting Officer     Acting Commissioner of Patents and Trademarks